United States Patent
Rollins, Sr. et al.

(10) Patent No.: US 10,792,421 B2
(45) Date of Patent: Oct. 6, 2020

(54) AUTOMATIC INSULIN DELIVERY SYSTEM WITH MINIMIZED INPUT VARIABLE LAG

(71) Applicant: Iowa State University Research Foundation, Inc., Ames, IA (US)

(72) Inventors: Derrick K. Rollins, Sr., Ames, IA (US); Yong Mei, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 296 days.

(21) Appl. No.: 15/725,604

(22) Filed: Oct. 5, 2017

(65) Prior Publication Data
US 2018/0099091 A1 Apr. 12, 2018

Related U.S. Application Data

(60) Provisional application No. 62/404,544, filed on Oct. 5, 2016.

(51) Int. Cl.
| | |
|---|---|
| *A61M 5/172* | (2006.01) |
| *A61K 38/28* | (2006.01) |
| *A61B 5/145* | (2006.01) |
| *A61P 5/48* | (2006.01) |
| *G16H 20/17* | (2018.01) |
| *G16H 50/50* | (2018.01) |
| *G16H 50/20* | (2018.01) |
| *A61M 5/142* | (2006.01) |
| *G05B 13/04* | (2006.01) |
| *G05B 17/02* | (2006.01) |

(52) U.S. Cl.
CPC ......... *A61M 5/172* (2013.01); *A61B 5/14532* (2013.01); *A61K 38/28* (2013.01); *A61M 5/142* (2013.01); *A61P 5/48* (2018.01); *G16H 20/17* (2018.01); *G16H 50/20* (2018.01); *G16H 50/50* (2018.01); *A61M 2005/14208* (2013.01); *A61M 2205/50* (2013.01); *A61M 2205/502* (2013.01); *A61M 2205/52* (2013.01); *G05B 13/048* (2013.01); *G05B 17/02* (2013.01)

(58) Field of Classification Search
CPC ...... A61M 5/172; A61M 5/142; G16H 20/17; G16H 50/50; G16H 50/20; A61B 5/14532; A61K 38/28
See application file for complete search history.

(56) References Cited

U.S. PATENT DOCUMENTS

| | | | |
|---|---|---|---|
| 6,544,212 B2 | 4/2003 | Galley et al. | |
| 8,273,052 B2 | 9/2012 | Damiano et al. | |
| 2010/0262117 A1 | 10/2010 | Magni et al. | |
| 2011/0098548 A1* | 4/2011 | Budiman | G06F 19/3456 600/365 |

OTHER PUBLICATIONS

Ding et al., Sensor Monitoring of Physical Activity to Improve Glucose Management in Diabetic Patients: A Review, Apr. 23, 2016, sensors, 16(589), p. 1-13 (Year: 2016).*
Schaepelynck et al., Advances in pump technology: insulin patch pumps, combined pumps and glucose sensors, and implanted pumps, 2011, Diabetes & Metabolism, 37, p. S85-S93 (Year: 2011).*
BodyMedia, BodyMedia SenseWear User Manual, 2014, BodyMedia, p. 1-27 (Year: 2014).*
Polar, RS800CX User Manual, Aug. 4, 2016, polar, p. 1-68 (Year: 2016).*
Turksoy et al., An Integrated Multivariable Artificial Pancreas Control System, 2014, Journal of Diabetes Science and Technology, 2014, 8(3), p. 498-507 (Year: 2014).*
Doyle, et al., "Glucose control strategies for treating type 1 diabetes mellitus", Journal of Process Control 17, pp. 572-576 (2007).
Marchetti, et al., "A Feedforward—Feedback Glucose Control Strategy for Type 1 Diabetes Mellitus", NIH Public Access, Author Manuscript, J Process Control, vol. 18(2), pp. 149-162, Feb. 2008.

* cited by examiner

*Primary Examiner* — John S Brusca
*Assistant Examiner* — Kaitlyn L Minchella
(74) *Attorney, Agent, or Firm* — McKee, Voorhees & Sease, PLC (57) ABSTRACT

This invention relates to automatic insulin delivery systems and methods of administering insulin. Preferably the systems and methods comprise a predictive feedforward control.

8 Claims, 6 Drawing Sheets

AUTOMATIC INSULIN DELIVERY SYSTEM WITH MINIMIZED INPUT VARIABLE LAG

TECHNICAL FIELD

This invention relates to automatic insulin delivery systems. In particular, the systems comprising a predictive feedforward control.

BACKGROUND OF THE INVENTION

In a person without diabetes, several systems including, for example, the metabolic, endocrine, and cardiovascular systems, function collectively to maintain homeostasis.

However, in a person with diabetes, the inherent glucose regulation mechanism is dysfunctional. Glucose levels are affected by the state of the metabolic-physiological-endocrine system. This includes factors such as insulin, stress, physical activity, hormonal levels, and fatigue. The effects of all these factors on blood glucose concentration (BGC) are highly complex and inter-related. In addition, factors such as food intake can cause glucose levels to change greatly and make glucose regulation and health management more difficult. These various factors are referred to as disturbances.

Insulin therapy involves multiple daily doses of insulin before meals or to correct high blood glucose, with the amount either pre-recommended by a physician or decided by the patient on the basis measured BGC and the number of carbohydrates they estimate will be ingested at the time of the meal. This protocol is inconvenient and unreliable. It often results in hypoglycemic and hyperglycemic episodes, both of which can be life-limiting and life-threatening. Thus, there has been a desire to develop more optimized insulin delivery systems and protocols. This has included research to develop automatic insulin delivery systems.

The potential for successful automatic insulin delivery has entered a new era due to recent technological advancements of insulin pumps and blood glucose sensors. However, for full automation and control capable of reducing the variance in BGC, the control algorithm must be capable of tight control for major disturbances such as meals, activity, and stress. Theoretically, the superiority of feedforward control (FFC) over all other control systems is that corrective action can be taken to cancel the effects of disturbances on the control variable (i.e., BGC) proactively. FFC has not been capable of addressing the complexity of various input disturbances impacting the regulation of blood glucose levels associated with diabetes due to inadequacy of effective model development of the complex causative relationships of disturbances and the controlled variable. This is insufficient as it fails to determine accurately the insulin infusion rate to substantially eliminate the effects of the modeled disturbances.

However, FFC even when coupled with other control models (e.g., feedback control), faces issues. For example, the effects of input variables are not instantaneous and there are often time delays associated with major inputs, such as meal ingestion and insulin infusion. Typically, the time delay associated meal ingestion is around half an hour, which indicates it takes roughly half an hour after a meal before BGC rise can be detected. Even for rapid-acting insulin, the time delay can be as much as 60 minutes. As a result of the difference in time delay, or dead time, a traditional FFC law can lead to an unrealizable feedforward controller. Therefore, the objective of this work is the development of a novel BGC control system that utilizes feedforward predictive control.

Consequently, there is a need for a system providing automatic delivery of insulin with minimal variability around the desired glucose target.

Accordingly, it is an objective of the claimed invention to provide a predictive feedfoward modeling network that presents a more phenomenological FFC law that predicts input dynamics, unmeasured pseudo-blood insulin and blood glucose dynamics and blood glucose levels.

Other objects, advantages and features of the present invention will become apparent from the following specification taken in conjunction with the accompanying figures.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF SUMMARY OF THE INVENTION

An advantage of the invention is a system and method for monitoring and delivering insulin automatically with minimal variability around the desired glucose target.

Therefore, it is a primary object, feature, and/or advantage of the invention to improve on and/or overcome the deficiencies in the art. It is a further object of the invention to provide an automatic insulin delivery system based on a feedforward predictive control. Other objects, features, and advantages of the invention can be identified by the description herein and the accompanying examples.

A preferred embodiment of the invention can be found in a method comprised of providing an insulin delivery system; providing a model to predict and determine an amount of insulin to administer, wherein the model is stored on a machine readable non-transitory media; providing predictive inputs and measured inputs to the model; parameterizing the model using the inputs to provide an output; and administering insulin using the insulin delivery system based on the output, wherein the administration of insulin proactively nullifies the effect of any disturbances on blood glucose concentration.

Still another preferred embodiment of the invention comprises a system for administering insulin, the system comprising an insulin delivery system comprising an apparatus for administering insulin; a plurality of sensors; a model stored on a machine readable non-transitory media associated with a computing device, the computing device in operative communication with the plurality of sensors; wherein the machine readable non-transitory media is capable of receiving predictive inputs and measured inputs and wherein the model parameterizes said predictive inputs and/or measured inputs to provide an output, wherein the output is computed by executing instructions by a processor of the computing device, wherein the computing device is in operable communication with the insulin delivery system. In a preferred embodiment, the sensors comprise one or more of a soft sensor, a remote sensor, an accelerometer, and a thermistor.

These and/or other objects, features, and advantages of the invention will be apparent to those skilled in the art. The invention is not to be limited to or by these objects, features and advantages. No single embodiment need provide each and every object, feature, or advantage. While multiple embodiments are disclosed, still other embodiments of the present invention will become apparent to those skilled in the art from the following detailed description, which shows

BRIEF DESCRIPTION OF THE FIGURES

FIGS. 6(A-C) show the results of $T_{ci}$ as the only disturbance in Example 2.

FIGS. 7(A-C) show the results of $T_{ci}$ and $C_{ai}$ as multiple disturbances.

Various embodiments of the present invention are described in detail with reference to the figures. The reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular insulin pumps, apparatuses for monitoring insulin and/or blood glucose levels, activity inputs, and stress measuring devices. It is further to be understood that all terminology used herein is for the purpose of describing particular embodiments only, and is not intended to be limiting in any manner or scope. For example, all units, prefixes, and symbols may be denoted in its SI accepted form.

Numeric ranges recited within the specification are inclusive of the numbers defining the range and include each integer, fraction, and decimal within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range such as 1, 2, 3, 4, 5, and 6, fractions such as 1¾, 3¼, and 4⅝, and decimals such as 2.3, 4.1, and 5.7. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Definitions

As used herein the singular forms "a," "an" and "the" can include plural referents unless the content clearly indicates otherwise.

As used herein the term "BIC" refers to blood insulin concentration. It is not limited to any particular measurement unit.

As used herein the term "BGC" refers to blood glucose concentration. It is not limited to any particular measurement unit.

As used herein the term "FBC" refers to feedback control or any synonyms thereof, including for example, "feed-back control."

As used herein the term "FBFF" refers to a feedback feedforward control.

As used herein the term "FFC" refers to feedforward control or any synonyms thereof, including for example, "feed-forward control" and "feed forward control."

As used herein the term "FFPC" refers to feedforward predictive control as defined by the present invention.

As used herein the term "glucose effectiveness" refers to insulin-independent effects, which include glucose-mediated simulation of glucose uptake and suppression of hepatic glucose output.

As used herein the term "remote insulin actions" refers to the insulin effect in organs that are not in quick equilibrium with the blood stream.

Feedfoward Predictive Control Model

The invention employs a semi-coupled network based on that which is proposed in U.S. Pat. Application No. 62/165, 283 filed on May 22, 2015 and entitled AUTOMATIC INSULIN DELIVERY SYSTEM, which is hereby incorporated in its entirety.

Utilizing the coupled feedforward control of the aforementioned application, the coupled structure in discrete form, with time delays is represented by Equations 1 and 2:

$$\hat{G}_t = \frac{a_1 \hat{v}_{1,t-m\Delta t}\Delta t + \hat{G}_{t-\Delta t}}{1 + \hat{a}_{GI}\hat{I}_t \Delta t} \quad (1)$$

$$\hat{I}_t = \frac{a_2 \hat{v}_{2,t-n\Delta t}\Delta t + \hat{I}_{t-\Delta t}}{1 + \hat{a}_I \Delta t} \quad (2)$$

where "G" is measured BGC at time, "t"; "a" represents estimateable model parameters; "v" is dynamic response of either ingested glucose or infused insulin at time, "t"; "mΔt" is the time delay between food ingestion and actual blood glucose increase; "$I_t$" is the unmeasured pseudo-BIC at time, "t"; "nΔt" is the time delay between insulin infusion and blood insulin increase; subscript "1" denotes food ingestion and "2" denotes insulin infusion.

Then at time t+nΔt, both equations become $$\hat{G}_{t+n\Delta t} = \frac{\hat{a}_1 \hat{v}_{1,t+(n-m)\Delta t}\Delta t + \hat{G}_{t+(n-1)\Delta t}}{1 + \hat{a}_{GI}\hat{I}_{t+n\Delta t}\Delta t} = G^{set} \quad (3)$$

$$\hat{I}_{t+n\Delta t} = \frac{\hat{a}_2 \hat{v}_{2,t}\Delta t + \hat{I}_{t+(n-1)\Delta t}}{1 + \hat{a}_I \Delta t} \quad (4)$$

Equation 3 can be rearranged to provide:

$$G^{set}(1+\hat{a}_{GI}\hat{I}_{t+n\Delta t}\Delta t) = \hat{a}_1 \hat{v}_{1,t+(n-m)\Delta t}\Delta t + \hat{G}_{t+(n-1)\Delta t} \quad (5)$$

Solving for I at t+nΔt using Equations 4 and 5

$$\hat{I}_{t+n\Delta t} = \frac{\frac{\hat{a}_1 \hat{v}_{1,t+(n-m)\Delta t}\Delta t + \hat{G}_{t+(n-1)\Delta t}}{G^{set}} - 1}{\hat{a}_{GI}\Delta t} = \frac{\hat{a}_2 v_{2,t}\Delta t + \hat{I}_{t+(n-1)\Delta t}}{1 + \hat{a}_I \Delta t} \quad (6)$$

Solving for $v_{2,t}$ $$v_{2,t} = \frac{\frac{1+\hat{a}_I\Delta t}{\hat{a}_{GI}\Delta t}\left(\frac{\hat{a}_1 \hat{v}_{1,t+(n-m)\Delta t}\Delta t + \hat{G}_{t+(n-1)\Delta t}}{G^{set}} - 1\right) - \hat{I}_{t+(n-1)\Delta t}}{\hat{a}_2 \Delta t} \quad (7)$$

Using Equation 7, $x_{2,t}$ can be obtained by reversing the transfer function from $v_{2,t}$ to $x_{2,t}$ $$x_{2,t} = G_2^{-1}(V_{2,t}) \quad (8)$$

Note that, $$\hat{I}_{t+(n-1)\Delta t} = \frac{\hat{a}_2 v_{2,t-\Delta t}\Delta t + \hat{I}_{t+(n-2)\Delta t}}{1 + \hat{a}_I \Delta t} \quad (9)$$

and $$\hat{G}_{t+(n-1)\Delta t} = \frac{\hat{a}_1 \hat{v}_{1,t+(n-m-1)\Delta t}\Delta t + \hat{G}_{t+(n-2)\Delta t}}{1 + \hat{a}_{GI}\hat{I}_{t+(n-1)\Delta t}\Delta t} \quad (10)$$

Then it can be shown $v_{2,t}$ is computed based on:

$$\hat{v}_{1,t+(n-m)\Delta t}$$

According to the present invention, when an insulin control device utilizes Equations 1-10 and when m<n, the control device will require future prediction of meal ingestion to determine the insulin feed rate (IFR) required. In a further embodiment of the invention, meal announcements are used which are equivalent to including a simple predictive model for meal timing, i.e., adding additional dead time to food ingestion. In an nonlimiting example, having meal announcements half an hour before a meal is essentially predicting meal size and/or contents 30 minutes in advance of the input and thus adding 30 minutes to dead time of the meal.

In a further embodiment of the invention and as one of skill in the art would appreciate, BGC is affected by many different disturbances. The three most significant non-invasive disturbances fall into one of three categories: stress, consumed energy (i.e., meals), and activities. To adequately control BGC through the feedforward predictive control method, each of these disturbances must be taken into account. Announcements of each could be included in order to predict the impact of each as previously discussed.

Figure 1:
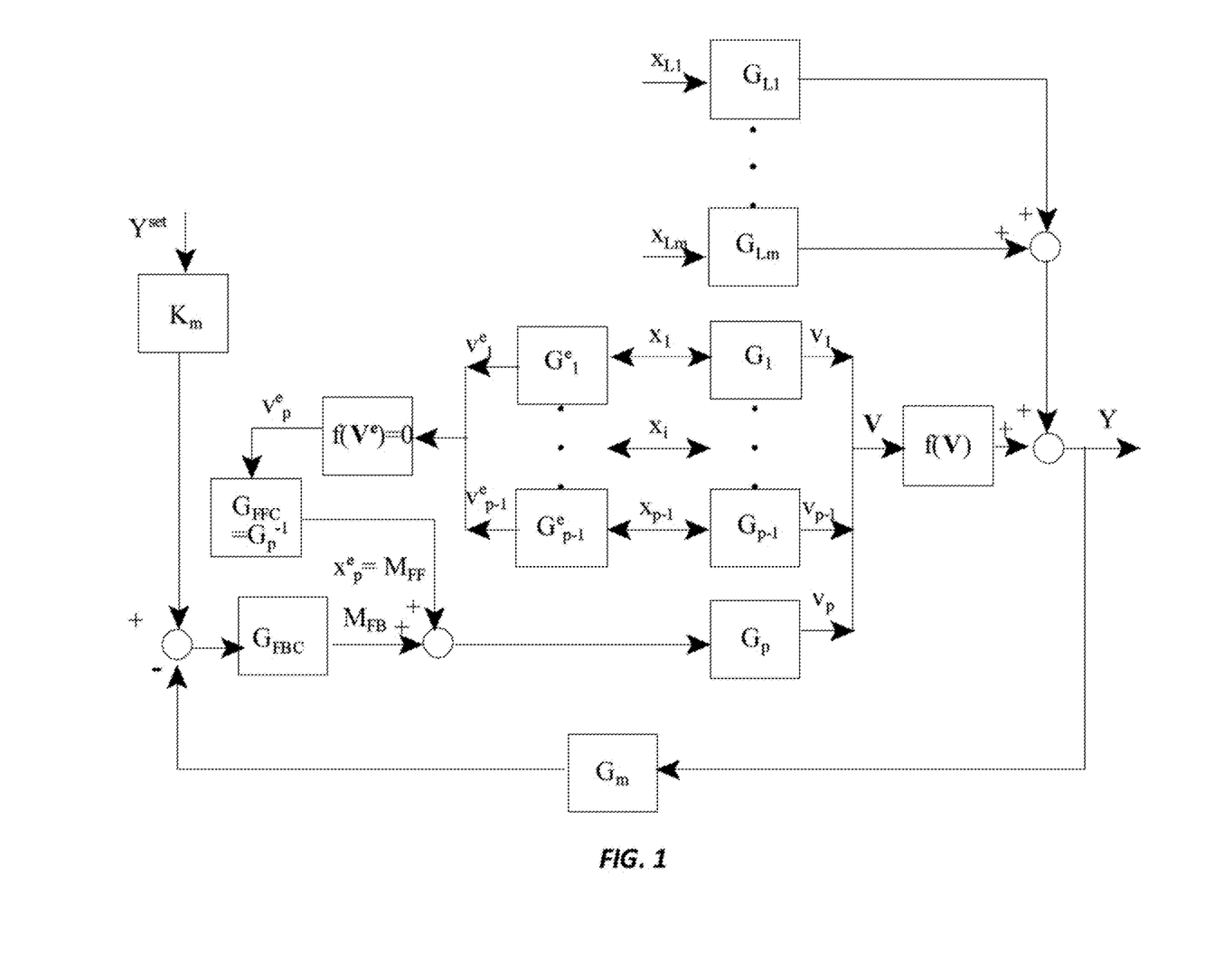
FIG. 1 is an exemplary block diagram for FBFF applied in Wiener model with m Loads and p FFC variables.

FIG. 1 shows an exemplary feedforward predictive control network of the invention, combined with feedback control, accounting for predicted and measured disturbances.

According to the present invention, FIG. 1 demonstrates the combination of feedforward control with feedback control, along with the presence of predictive announcements. "Y" in FIG. 1 represents BGC; "$Y^{set}$" denotes the set point for BGC; "$x_{11}$" to "$x_{1m}$" represent unmeasured disturbances that affect the system (i.e. human bodies); "$x_1$" to "$x_{p-1}$" represent measured input variables (e.g. physical activities, and meal logs); "$x_p$" denotes IFR, all "v's" are dynamic effects of corresponding "x" inputs; and "$M_{FF}$", "$M_{FB}$" are computed by feedforward/feedback controller, combined into a manipulated variable-IFR. "$G_{11}$" to "$G_{1m}$" represent load blocks; "$G_1$" to "$G_p$" represent dynamic block for each input; superscript "e" denotes estimate of corresponding variable; "$G_m$" is measurement block; "$K_m$" is system gain; "$G_{FFC}$" is the controller block for feedforward control; and "$G_{FBC}$" is the controller block for feedback control.

Insulin

There are two types of insulin manipulation: basal and bolus. Basal insulin, often referred to as background insulin, functions to keep blood glucose levels consistent during periods of fasting. Basal insulin can be provided by the continuous administration of fast-acting insulin in small doses. Bolus insulin functions to control BGC for disturbances. It can be administered intravenously, by intramuscular injection, by intrathecal injection, or by subcutaneous injection.

Activities

There are many activities that affect BGC. These activities include, but are not limited to, exercise, walking, working, and casual movement. These activities can be monitored by monitoring and/or measuring body position, movement, heat dissipated, skin temperature, near body temperature, galvanic skin response, and sleep. In order to monitor body position and movement, it is preferable to use a two-axis accelerometer. Sleep can be monitored by the lack of certain kinds of movement. The heat dissipated from the body can be accounted for based on the body's heat flux. Skin temperature and near-body temperature can be measured by sensitive thermistors. Galvanic skin response (GSR) can be measured by the conductivity of a person's skin as it varies due to physical and emotional stimuli.

Any type and number of monitoring systems can be used to monitor the various activities. In a preferred embodiment, a single monitoring system is employed to monitor all activities at once. A preferred monitoring system is a type similar to the SenseWear® Pro3 Body Monitoring System, previously available from BodyMedia, Inc. in Pittsburgh, Pa.

Feedback-Feedforward Control

In a preferred embodiment, the semi-coupled network is used in a FBFF process control scheme. This is because FFC proactively nullifies measured modeled disturbances prior to the disturbance affecting the system. FBC addresses unmeasured disturbances, modeling and measurement errors. Thus, in the context of BGC, it is ideal to employ a process control having both FFC and FBC. This will provide a process control capable of both nullifying measured disturbances before they affect the system and compensating for any disturbances not adequately handled by FFC.

Method of Controlling Insulin

The process control of the invention can be employed in the monitoring and regulation of BGC for patients, particularly patients suffering from type 1 diabetes mellitus. The process control scheme of the invention employs an insulin delivery system 4, a computing device 8 comprising a processor 10, machine readable non-transitory media 12 which stores the coupled-model 14 of the invention, and a monitoring system 2.

Figure 2:
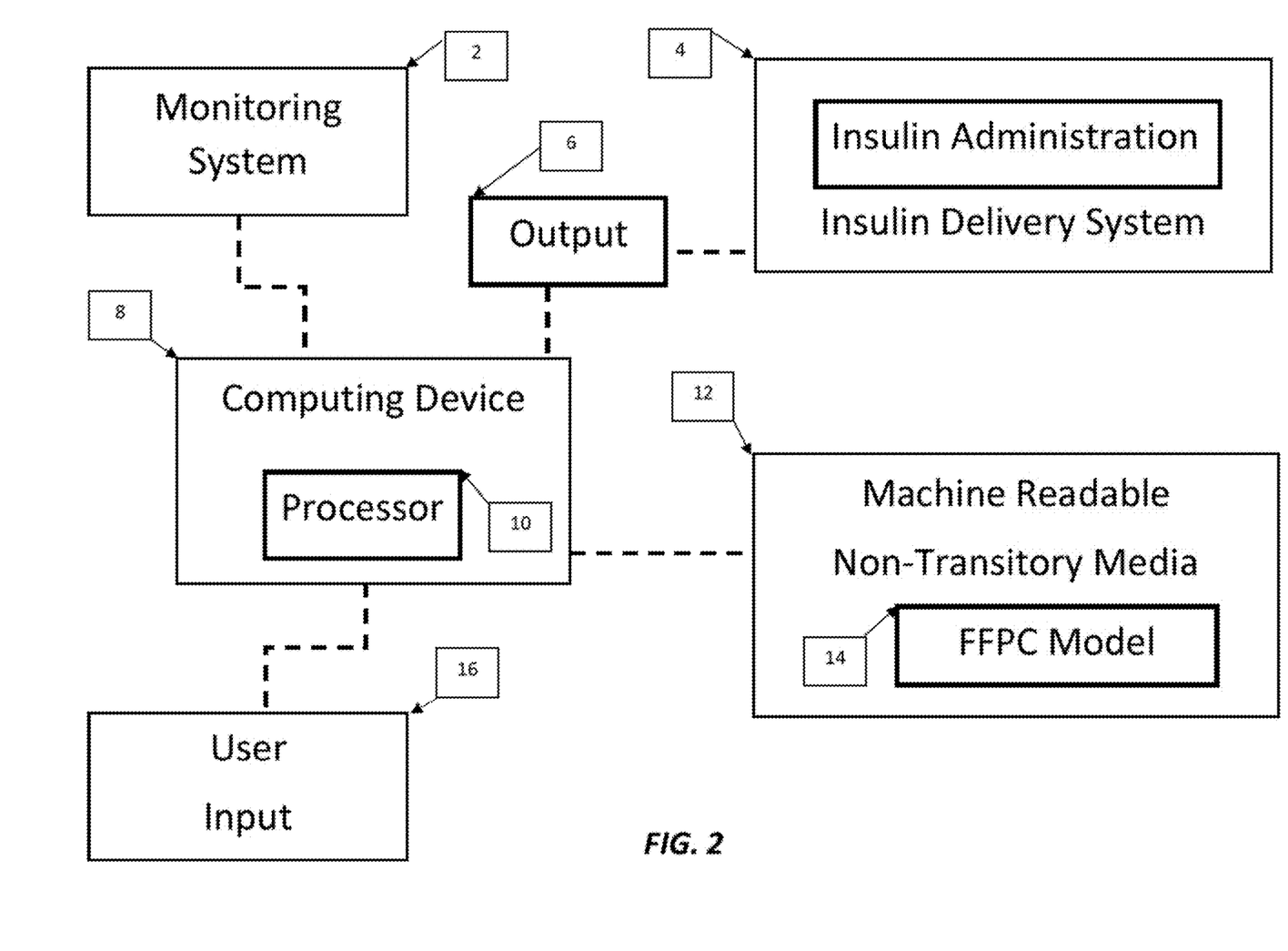
FIG. 2 shows a diagram of a system or method for controlling BGC according to the invention.
Figure 3:
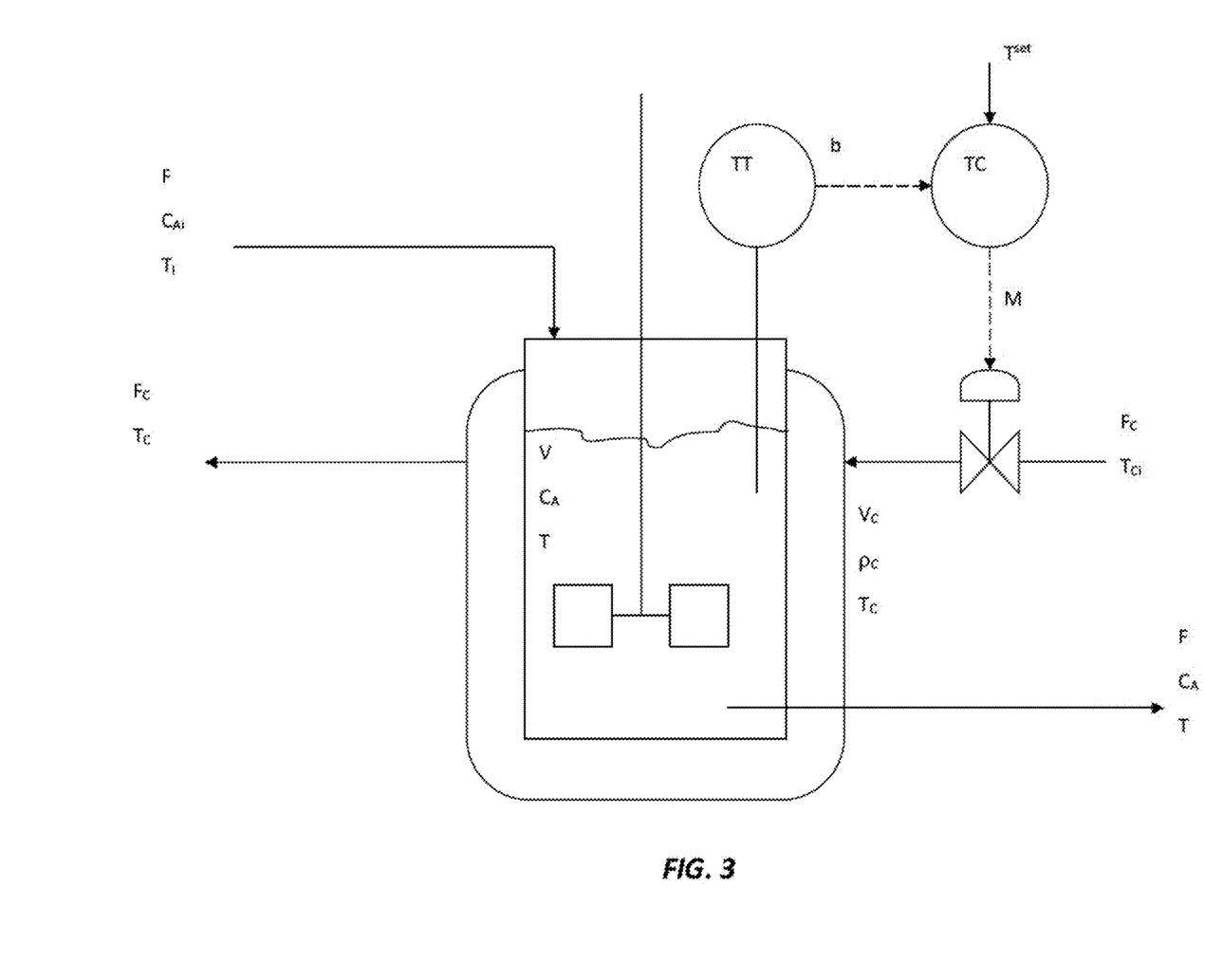
FIG. 3 shows the model CSTR used for Examples 1-3.

FIG. 2 shows an exemplary method of controlling BGC according to the invention. The method employs a monitoring system 2, which monitors the various inputs (disturbances). For example, the monitoring system can provide information regarding the activity inputs ($X_A$ in FIGS. 2 and 3), such as, skin temperature, near body temperature, and galvanic skin response. The monitoring system 2 can comprise one or more sensors capable of monitoring one of more of the inputs. In an aspect of the invention, the system can include a soft or virtual sensor monitoring, such as, heat flux. In an embodiment of the invention, the patient's basal and bolus are known from the insulin pump 2. For example, as bolus insulin can be administered by the insulin delivery system 4 and as the amount can be directed by the computing device 8, the amount of bolus insulin can be automatically logged.

As shown in FIG. 2, both the user input 16 and monitoring system 2 are in operable communication with a computing device 8 that contains a processor 10. The computing device 8 is also in operable communication with a machine readable non-transitory media 12. The machine readable non-transitory media 12 can store the FFPC model 14. The inputs 16, 2 are parameterized by the FFPC model 14 to provide an output 6 that directs the insulin delivery system 4. It is to be understood that wireless transceivers may be used to communicate information from sensors to the computing device 8. The sensors may be associated with wearable devices, mobile devices, or other computing devices.

FIG. 2 shows the computing device 8 is also in operable communication with an insulin delivery system 4. The insulin delivery system 4 can comprises an apparatus suitable for administering insulin. Any suitable apparatus for administering insulin can be employed, including, but not limited to, an automatic insulin pump, a remotely controlled insulin pump, an IV, or a catheter. Any suitable insulin pump capable of communication with the control system can be used. Preferably, the control method of the invention is uses a remotely controlled insulin pump. Selection of an insulin pump can be based on preferences of the user for other features. The user inputs 16 and inputs provided by the monitoring system 2 are parameterized by the model 14 stored on the machine readable non-transitory media 12, which is in operable communication with the computing device 8. The model 14 provides an output to the computing device 8 which in turn provides an output 6 (as shown in FIG. 2) to the insulin delivery system 4, which can direct the insulin delivery system 4 to nullify and/or compensate for predicted disturbances via the feedforward predictive control scheme. In some embodiments of the invention, the output 6 can be provided in any communicable form and recorded, printed, displayed, etc. such that there is a record of the output 6. In an embodiment of the invention where the basal and bolus insulin are automatically monitored the output 6 can be relayed back into the machine readable non-transitory media 12.

Embodiments of the invention can reduce the variance in blood glucose concentration of a patient by proactively nullifying one or more disturbances on the patient's blood glucose system. In embodiments of the invention, when compared with existing methods of controlling blood glucose concentration, the reduction in variance can be greater than 50%, preferably greater than 60%, and more preferably greater than 70%.

EXAMPLES

Embodiments of the present invention are further defined in the following nonlimiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Utilizing a continuous stirred tank reactor (CSTR) as a process model, the methods of the present invention were tested. A CSTR model was selected as its coupled network bears resembles the structure between carbohydrate amount ingested and IFR as shown in Equations 11 and 12:

$$\frac{dG}{dt} = -\{S_G + X(t)\}G \tag{11}$$

$$\frac{dX}{dt} = p_2 I(t) - p_3 X(t) \tag{12}$$

where "G" represents BGC (mg/dl); "I" represents BIC (unit/di); "X(t)" denotes remote insulin actions (1/min); "SG" denotes glucose effectiveness (1/min); "$p_2$" represents fractional appearance rate of insulin in interstitial fluids; and "$p_3$" represents fractional clearance rate of insulin in interstitial fluids. Both $p_2$ and $p_3$ are estimable parameters.

In comparison, the CSTR process shown in FIG. 2 is described by Equations 13-18.

$$\frac{dC_A}{dt} = \frac{F}{V}(C_{Ai} - C_A) - kC_A^2 \tag{13}$$

$$\frac{dT_T}{dt} = \frac{F}{V}(T_T - T_T) - \frac{\Delta H_R}{\rho C_p} kC_A^2 - \frac{UA}{\rho V C_p}(T_T - T_C) \tag{14}$$

$$\frac{dT_C}{dt} = \frac{UA}{V_C \rho_C C_{pC}}(T_T - T_C) - \frac{F}{V_C}(T_C - T_{Ci}) \tag{15}$$

$$k = k_0 exp\left(\frac{-E}{R(T_T + 273.16)}\right) \tag{16}$$

$$F_C = F_{Cmax} \times a^{(-M)} \tag{17}$$

$$f(\hat{V}_t) = \hat{a}_0 + \hat{a}_1 \hat{v}_{1,t-m\Delta t} + \hat{a}_2 \hat{v}_{2,t-n\Delta t} + \hat{a}_3 \hat{v}_{3,t-p\Delta t} + \tag{18}$$
$$\hat{a}_{12} \hat{v}_{1,t-m\Delta t} \hat{v}_{2,t-n\Delta t} + \hat{a}_{13} \hat{v}_{1,t-m\Delta t} \hat{v}_{3,t-p\Delta t} + \hat{a}_{11} \hat{v}_{1,t-m\Delta t}^2 + \hat{a}_{33} \hat{v}_{3,t-p\Delta t}^2$$

Definitions of variables and accompanying units are shown in Table 1.

TABLE 1

| Variable | Definition | SS Value (units) |
|---|---|---|
| A | Heat transfer area | 5.40 (m$^2$) |
| α | Control valve rangeability parameter | 50 (none) |
| $C_A$ | Concentration of species A in reactor | 1.0302 (kgmol/m$^3$) |
| $C_{Ai}$ | Concentration of species A in inlet stream | 2.88 (kgmol/m$^3$) |
| $c_p$ | Heat capacity of feed and product streams | 1.815 × 10$^5$ (J/kgmol-° C.) |
| $c_{pc}$ | Heat capacity of coolant | 4184 (J/kg-° C.) |
| $\Delta H_R$ | Heat of reaction | −9.86 × 10$^7$ (J/kgmol) |
| E | Activation energy | 1.182 × 10$^7$ (J/kgmol) |
| F | Feed flow rate | 0.45 (m$^3$/s) |
| $F_C$ | Coolant flow rate | 0.44 (m$^3$/s) |
| $F_{Cmax}$ | Maximum flow rate of coolant through control valve | 1.2 (m$^3$/s) |
| K | Reaction rate constant | 0.09 (m$^3$/s-kgmol) |
| $k_0$ | Arrhenius frequency parameter | 0.0744 (m$^3$/s-kgmol) |
| M | Input signal to the valve | 0.26 (none) |
| R | Gas law constant | 8314.39 (J/kgmol-K) |
| ρ | Density of reactor content | 19.2 (kgmol/m$^3$) |
| $\rho_c$ | Density of coolant | 1000 (kg/m$^3$) |
| $T_c$ | Coolant temperature in the jacket | 50.48 (° C.) |
| $T_{Ci}$ | Coolant inlet temperature | 27 (° C.) |
| T | Reactor temperature | 88 (° C.) |
| $T_m$ | Measured reactor temperature | 88 (° C.) |
| U | Overall heat transfer coefficient | 2.13 × 10$^5$ (J/s-m$^2$-° C.) |
| $V_C$ | Cooling jacket volume | 1.82 (m$^3$) |
| V | CSTR volume | 7.08 (m$^3$) |

Then, applying the methods of the present invention, the input signal to valve, $M_{ff}$, can be determined by Equations 19-21.

$$\hat{v}_{1,t} = \frac{-b + \sqrt{b^2 - 4ac}}{2a} \quad (19)$$

where $$a = \hat{a}_{11}, b = \hat{a}_1 + \hat{a}_{12}\hat{v}_{2,t+(m-n)\Delta t} + \hat{a}_{13}\hat{v}_{3,t+(m-p)\Delta t} \quad (20)$$

and $$c = \hat{a}_0 + \hat{a}_2\hat{v}_{2,t+(m-n)\Delta t} + \hat{a}_3\hat{v}_{3,t+(m-p)\Delta t} + \hat{a}_{33}\hat{v}_{3,t+(m-p)\Delta t}^2 \quad (21)$$

Therefore, $$M_{ff} = \hat{x}_{1,t} = \hat{\tau}_1 \frac{\hat{v}_{1,t} - \hat{v}_{1,t-\Delta t}}{\Delta t} + \hat{v}_{1,t} \quad (22)$$

The time delay associated with the input signal, $v_1$, is 10 minutes, while time delays with dynamic $T_{ci}$ ($v_2$) and dynamic $C_{ai}$ ($v_3$) are both five minutes. In order to apply the present invention while manipulating the input variable, future predictions on $T_{ci}$ and $C_{ai}$ are required. However, according to methods of the present invention, by having announcements 5 minutes in advance for each of $T_{ci}$ and $C_{ai}$, the methods of the present invention are effectively implemented.

Example 2

Figure 4:
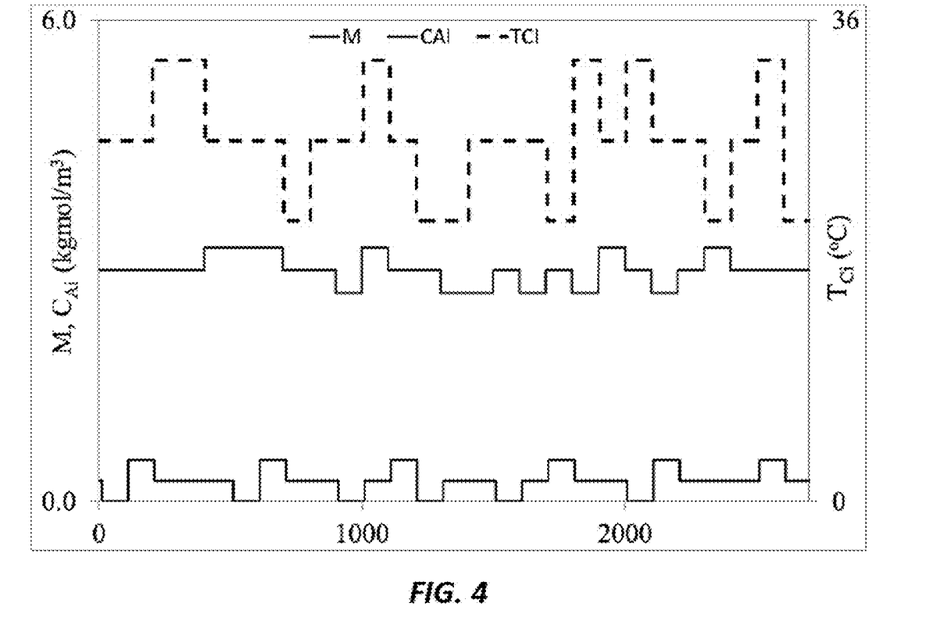
FIG. 4 shows the generation of three input variables by sequential step tests as utilized in Example 2.

Applying the methods of Example 1, three input variables of input signal to valve, M (x1); temperature of inlet coolant flow, $T_{ci}$ (x2); and concentration of component A in inlet flow, $C_{ai}$ (x3) were generated by sequential step tests as shown in FIG. 4. One output for this study is the measured tank temperature, $T_m$.

Figure 5:
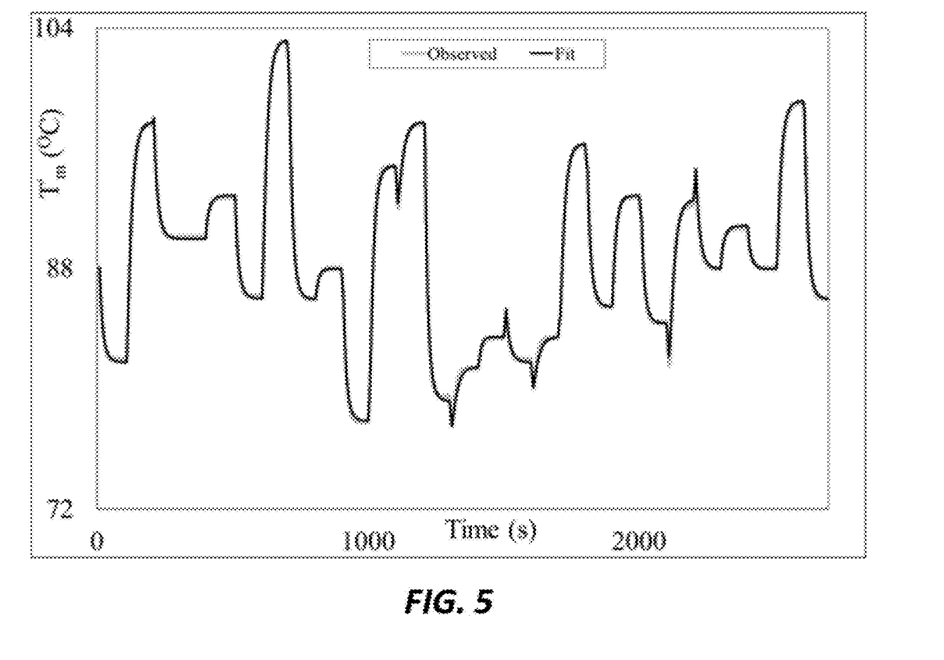
FIG. 5 shows the fitted tank temperature collected in Example 2 by implementing time delay into a Wiener model.

To identify the parameters of the methods of the present invention as contained within a Wiener model, training with 2700 minutes of simulation data was first conducted. With time delay implemented into a Wiener model, fitted tank temperature was collected and is shown in FIG. 5. With model parameters isolated, the effects of the present invention were examined by minimizing the variation of tank temperature around its set point of 88° C. by manipulating input signal to valve M. In particular, the effects of one disturbance, $T_{ci}$ was examined. When announcement for the disturbance was done, the Equation 19 was used. Otherwise, the most recent recorded value for the disturbance was implemented.

A proportional-integral (PI) feedback controller was implemented in conjunction with a feedforward controller to form the controller of the present invention. For this controller, $K_C$=1.40, I=11.0 and M=$M_{fb}$, where $M_{fb}$ is the signal from the PI controller to the valve. As a result, the controller of the present invention can be described as Equation 23:

$$M = M_{fb} + M_{ff} \quad (23)$$

Figure 6A:
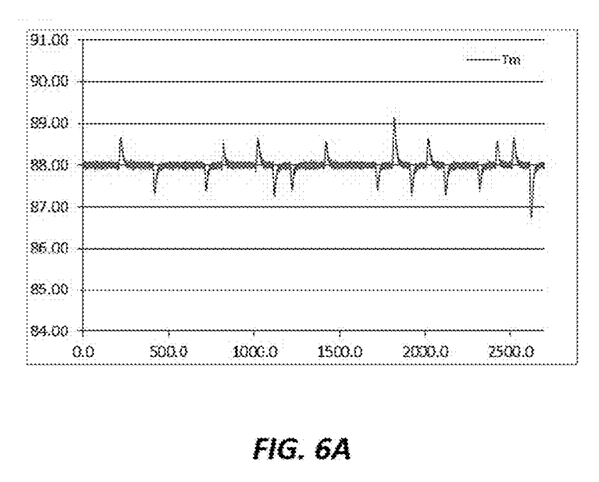
FIG. 6A represents the tank temperature under feedback control alone.
Figure 6B:
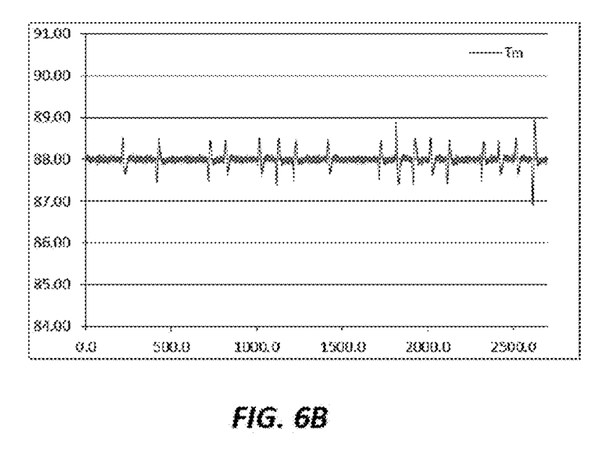
FIG. 6B represents the tank temperature by applying the methods of the present invention without the announcement of changing $T_{ci}$.
Figure 6C:
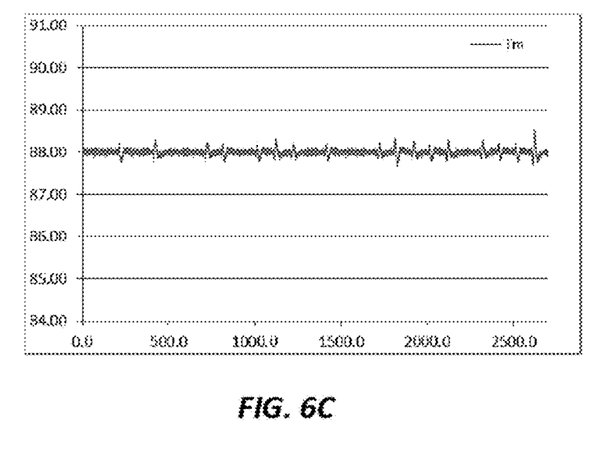
FIG. 6C represents the tank temperature by applying the methods of the present invention with announcement of future $T_{ci}$.

Results of $T_{ci}$ as the only disturbance are shown in FIG. 6A, 6B, 6C. FIG. 6A represents the tank temperature under feedback control alone. FIG. 6B represents the tank temperature by applying the methods of the present invention without the announcement of changing $T_{ci}$. FIG. 6C represents the tank temperature by applying the methods of the present invention with announcement of future $T_{ci}$. As shown, the variation of tank temperature around its set point (i.e., standard deviation) is reduced by applying the methods of the present invention even without from $T_{ci}$ announcement by approximately 20%. With the inclusion of announcement, the reduction in variation increases to approximately 63%. These results indicate that the further improvement in variation reduction by utilizing the present invention and demonstrates the importance of incorporating time delay/dead time into processes.

Example 3

Figure 7A:
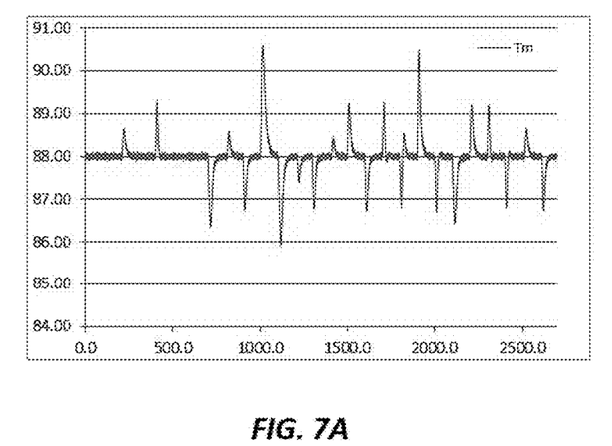
FIG. 7A represents the tank temperature under feedback control alone.
Figure 7B:
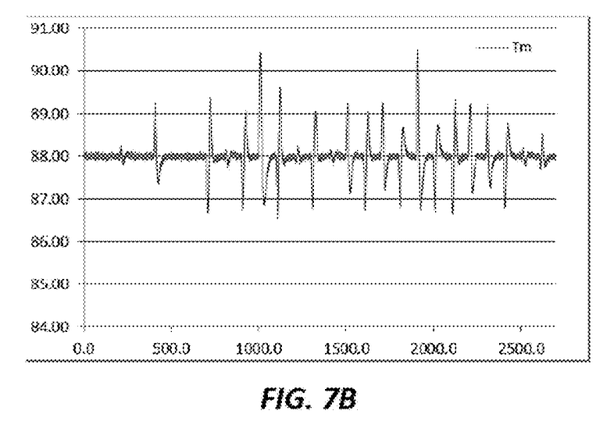
FIG. 7B represents the tank temperature by applying the methods of the present invention with the announcement of changing $T_{ci}$, but without the announcement of changing $C_{ai}$.
Figure 7C:
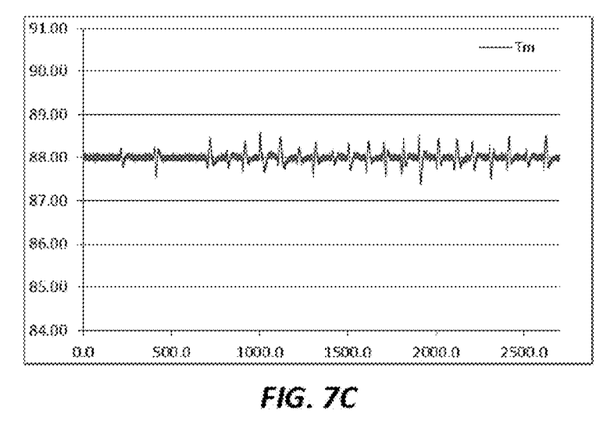
FIG. 7C represents the tank temperature by applying the methods of the present invention with announcement of future $T_{ci}$ and $C_{ai}$.

Applying the methods of Example 2, the effects of multiple disturbances were examined, i.e., disturbances of $T_{ci}$ and $C_{ai}$. The results achieved according to the methods of Example 2 are shown in FIG. 7A, FIG. 7B, and FIG. 7C. FIG. 7A represents the tank temperature under feedback control alone. FIG. 7B represents the tank temperature by applying the methods of the present invention with the announcement of changing $T_{ci}$, but without the announcement of changing $C_{ai}$. FIG. 7C represents the tank temperature by applying the methods of the present invention with announcement of future $T_{ci}$ and $C_{ai}$.

As shown, the variation of tank temperature around its set point is only slightly reduced by applying the methods of the present invention without announcement of $C_{ai}$ (but still with $T_{ci}$ announcement) by a proportion of about 8%. When applying the methods of the present invention with both $T_{ci}$ and $C_{ai}$ announcement, the reduction in set point variation increases to about 74%. The results further demonstrate that the Wiener structure can be easily extended to multivariable structures and the present invention can be expanded to multivariable control. Further, the results indicate that without $C_{ai}$ announcement, the reduction in variation is not significant when compared to the reduction seen with multivariable announcement.

Therefore, methods and systems have been described relating to insulin delivery. It should be understood that the present invention contemplates numerous variations, options, and alternatives. For example, where sensed information is provided as input, the sensed information may be supplied from any number of sensors including sensors associated with wearable devices, mobile devices, or other computing devices. Where information is input by users, it is to be understood that the information may be input using wearable devices, mobile devices, or other computing devices including the same device used for insulin delivery. It is further to be understood that the model may be stored on any number of computing devices including a mobile device, or the same device used for insulin delivery.

The above specification provides a description of the manufacture and use of the disclosed compositions and methods. Since many embodiments can be made without departing from the spirit and scope of the invention, the invention resides in the claims.

What is claimed is:

1. A method comprising steps of:
   providing an insulin delivery system;
   providing a model to predict and determine an amount of insulin to administer, the model stored on a machine readable non-transitory media associated with a computing device;
   providing predictive inputs and measured inputs to the model;
   parameterizing the model using the inputs to provide an output;
   computing the output from the model by executing instructions using a processor of the computing device; and
   administering insulin using the insulin delivery system based on the output, wherein the administration of insulin proactively nullifies the effect of any disturbances on blood glucose concentration,
   wherein the model includes the feedforward predictive control law of $$\hat{I}_{t+(n-1)\Delta t} = \frac{\hat{a}_2 v_{2,t-\Delta t}\Delta t + \hat{I}_{t+(n-2)\Delta t}}{1+\hat{a}_I \Delta t};$$

$$\hat{G}_{t+(n-1)\Delta t} = \frac{\hat{a}_1 \hat{v}_{1,t+(n-m-1)\Delta t}\Delta t + \hat{G}_{t+(n-2)\Delta t}}{1+\hat{a}_{GI}\hat{I}_{t+(n-1)\Delta t}\Delta t};$$

$$x_{2,t} = G_2^{-1}(V_{2,t}).$$

2. The method of claim 1 wherein one or more of said measured inputs are provided by an automatic monitoring system.

3. The method of claim 1 wherein one or more of said predictive inputs are provided manually by a user.

4. The method of claim 2 wherein the automatic monitoring system comprises one or more sensors.

5. The method of claim 2 wherein the automatic monitoring system monitors at least one of the following variables body position, movement, heat dissipated, skin temperature, near body temperature, galvanic skin response, and sleep, basal insulin, or bolus insulin.

6. The method of claim 4 wherein the one or more sensors comprise at least one of the following a soft sensor, a remote sensor, an accelerometer, or a thermistor.

7. The method of claim 3 wherein the one or more inputs provided manually by the user includes at least one of the following consumed energy, basal insulin, or bolus insulin.

8. The method of claim 1 wherein the insulin delivery system comprises an apparatus for administering insulin.

* * * * *